(12) United States Patent
Windolf (10) Patent No.: US 10,772,557 B2
(45) Date of Patent: Sep. 15, 2020

(54) KIT FOR ASSEMBLING A MEDICAL DEVICE PROVIDED WITH DATA ACQUISITION MEANS

(71) Applicant: AO Technology AG, Chur (CH)

(72) Inventor: Markus Windolf, Chermside West (AU)

(73) Assignee: AO Technology AG, Chur (CH)

( * ) Notice: Subject to any disclaimer, the term of this patent is extended or adjusted under 35 U.S.C. 154(b) by 162 days.

(21) Appl. No.: 15/565,972

(22) PCT Filed: Apr. 27, 2015

(86) PCT No.: PCT/CH2015/000062
§ 371 (c)(1),
(2) Date: Oct. 12, 2017

(87) PCT Pub. No.: WO2016/172806
PCT Pub. Date: Nov. 3, 2016

(65) Prior Publication Data
US 2018/0055444 A1 Mar. 1, 2018

(51) Int. Cl.
*A61B 5/00* (2006.01)
*A61B 5/103* (2006.01)
(Continued)

(52) U.S. Cl.
CPC .......... *A61B 5/4851* (2013.01); *A61B 5/0031* (2013.01); *A61B 5/01* (2013.01);
(Continued)

(58) Field of Classification Search
CPC ......... A61B 5/4851; A61B 5/01; A61B 5/076; A61B 17/80; A61B 5/686; A61B 5/103;
(Continued)

(56) References Cited

U.S. PATENT DOCUMENTS 8,486,070 B2 7/2013 Morgan et al.
2008/0154265 A1* 6/2008 Duda .................. A61B 5/076
606/70

(Continued)

FOREIGN PATENT DOCUMENTS

WO 2006055547 A2 5/2006
WO 2008103181 A1 8/2008
WO 2010142045 A1 12/2010

*Primary Examiner* — Eric F Winakur
*Assistant Examiner* — Abid A Mustansir
(74) *Attorney, Agent, or Firm* — Rankin, Hill & Clark LLP (57) ABSTRACT

Kit for assembling an implantable medical device (30) provided with a data acquisition device (1), the kit comprising: a medical implant (100); a data acquisition device (1) which includes: one or more sensors (5); an electronic data processing device (2) electrically connectable or connected to the one or more sensors (5); a data memory (16); a data transmission device (4); and a biocompatible sterilisable housing (9) encapsulating at least the data processing device (2), the data memory (16) and the data transmission device (4); wherein the housing (9) comprises means (10) for releasably affixing the housing (9) to the implant (100), the data processing device (2) is programmed to calculate statistical data based on measurement data received from the one or more sensors (5) and to store the statistical data in the data memory (16); and wherein the one or more sensors (5) are either arranged in the housing (9); or the one or more sensors (5) are separately fixable to the implant (100) in a selected position.

20 Claims, 4 Drawing Sheets

(51) Int. Cl.
*A61B 5/01* (2006.01)
*A61B 5/07* (2006.01)
*A61B 17/80* (2006.01)

(52) U.S. Cl.
CPC .............. *A61B 5/076* (2013.01); *A61B 5/103* (2013.01); *A61B 5/686* (2013.01); *A61B 17/80* (2013.01); *A61B 5/4504* (2013.01); *A61B 5/6878* (2013.01); *A61B 2560/0214* (2013.01); *A61B 2562/0219* (2013.01); *A61B 2562/0247* (2013.01); *A61B 2562/0252* (2013.01); *A61B 2562/0261* (2013.01); *A61B 2562/162* (2013.01)

(58) Field of Classification Search
CPC .......... A61B 5/0031; A61B 2562/0261; A61B 2562/0247; A61B 2562/0252; A61B 2562/162; A61B 2562/0219; A61B 2560/0214; A61B 5/4504; A61B 5/6878
See application file for complete search history.

(56) References Cited

U.S. PATENT DOCUMENTS

| | | | |
|---|---|---|---|
| 2009/0222050 A1* | 9/2009 | Wolter | A61B 5/0031 606/286 |
| 2010/0152621 A1* | 6/2010 | Janna | A61B 5/0031 600/595 |
| 2011/0213225 A1* | 9/2011 | Bernstein | G06Q 50/22 600/309 |
| 2012/0123221 A1* | 5/2012 | Windolf | A61B 5/0031 600/300 |
| 2013/0190654 A1 | 7/2013 | Deirmengian et al. | |
| 2013/0338455 A1 | 12/2013 | Gradel et al. | |

\* cited by examiner

KIT FOR ASSEMBLING A MEDICAL DEVICE PROVIDED WITH DATA ACQUISITION MEANS

BACKGROUND OF THE INVENTION

1. Field of the Invention

The invention relates to a kit for assembling a medical device provided with a data acquisition device according to the preamble of claim 1 and to a method for monitoring and/or controlling medical implants according to the preamble of claim 36.

2. Description of the Related Art

Monitoring and controlling of medical implant behaviour for fracture fixation has become more and more important. The measurement of implant parameters as strain, displacement, and transferred force provides valuable information about the process of bone healing. Current wireless techniques allow only short measurements providing restricted information or need to transfer huge amounts of data from the implanted measurement device to an external receiver. From U.S. Pat. No. 8,486,070 MORGAN ET AL. a telemetric orthopedic implant is known which includes sensors allowing measurement of the applied mechanical load across the implant. This known implant additionally comprises a microprocessor, one or more memory devices, a power supply and data communication components. The sensors and associated electronic components are located in one or more recesses on the surface of the implant and covered therein with a biocompatible potting material. The electronic components transmit data received from the sensor by wire or through wireless communication to an external data receiver which in turn is connected to an external computing device either by wires or wirelessly. A disadvantage of this known device is that the sensors and electronic components are integrated in the implant so that a variety of different implants is needed to take account of different desired sensor positions.

BRIEF SUMMARY OF THE INVENTION

It is an object of the invention to provide a kit for assembling an implantable medical device provided with a data acquisition device which is suitable for monitoring and/or controlling an implant and which permits to obtain long term measurements of relevant parameters and data transmission under minimal energy consumption and minimal required space of the implanted data acquisition device.

The invention solves the posed problem with a kit for assembling a medical device provided with a data acquisition device comprising the features of claim 1 and with a method for monitoring and/or controlling medical implants comprising the features of claim 36.

The advantages of the kit according to the invention can be essentially seen therein that:

due to the releasable connection between the implant, the sensor and the data acquisition device standard implants can be used. The manufacturing processes of the implants do not have to be adapted for the use of integrated data acquisition devices;

the surgeon can spontaneously decide during the operation whether a sensor and/or a data acquisition device shall be implanted;

the sensor can be positioned with consideration of the anatomy and/or a bone fracture;

there is no need to manufacture similar implants having differently positioned sensors and/or data acquisition devices;

the data acquisition device and/or the sensor can be removed through a stab incision without explanting the implant; and the data to be transmitted can be significantly reduced, e.g. to an amount of 200 kB during a working life of the battery of between four and twelve months depending on the configuration of the device. A power save mode can be applied to reduce the data collection to 4-6 h during the day. Thus, the energy consumption for data transmission can be reduced which usually is the major part of the energy demand of the device so that an autonomous operation of the device during at least four months can be achieved, with consideration of the size restrictions in the patient's body (e.g. using a battery: 3V round cell with a capacity of 50 mAh);

due to the reduction of the data to be transmitted low energy wireless technology standards can be used, e.g. Bluetooth Low Energy so that energy consumption is kept low and a commercial receiver, such as a smartphone can be used as an external data receiver and no specific electronic devices are needed. Furthermore, remote data monitoring is possible, the patient does not have to go to the clinic for data inquiry and download. Choice of the time-points for download is uncritical; and long term measurements which are most relevant for gaining information about bone healing can be performed by detecting peaks from a sensor response during physiological loading/unloading, summing up amplitudes and transferring only the sum, the number of cycles and the current sensor value to a wireless receiver outside of the patient. Long term measurement further eliminates natural variances in physiological loading rendering a reference measurement, such as ground reaction force assessment or a second reference sensor as known from US 2013/0190654 unnecessary. Furthermore, it becomes possible to assess patient activity over the day cycle in terms of number of steps taken and their distribution in terms of loading intensity. Moreover, long term measurement allows capturing of unbiased natural locomotion as occurring in the patient's familiar environment as opposed to artificial activity in the gait lab.

Further advantageous embodiments of the invention can be commented as follows:

In a special embodiment the data processing device is programmed for continuous data collection within a selectable period of time so as to permit the advantage that the measurement data can be continuously obtained during a selectable period of time. In another embodiment the data acquisition device additionally includes an internal clock. By this means the advantage can be achieved that time points for data capture can be synchronized to the day cycle e.g. only 4 h data capture during midday or excluding sleeping periods of 4-8 hours during the night to save energy.

In a further embodiment the data processing device is programmed to calculate the statistical data by using evaluation intervals of minimum 4 hours, preferably of minimum 6 hours.

In a further embodiment the data processing device is programmed to calculate the statistical data by using evaluation intervals of maximum 48 hours, preferably of maximum 24 hours. Due to the above ranges for the evaluation intervals the data to be transmitted can be minimized.

In a further embodiment the data processing device is programmed to automatically calculate the statistical data in selectable evaluation intervals.

In another embodiment the housing is made of a biocompatible but non-biodegradable metallic or polymeric material, preferably of polyetheretherketone (PEEK) or polyetherketoneketone (PEKK).

In another embodiment the data transmission device is configured as a wireless data transmitter based on a wireless technology standard, preferably Bluetooth, RFID or NFC. If the Bluetooth or NFC standard is used the external data receiver can be a commercially available smartphone. Contrarily to known devices a proprietary communication system is not necessary because the personal smartphone of the patient which includes a wireless internet connection can be used.

In again another embodiment the data transmission device is actuatable to transmit selected data stored in the data memory by means of an external data receiver.

In a further embodiment the data processing device is programmable via an external data receiver.

In a further embodiment the data acquisition device further comprises a power supply. Preferably, the power supply is one of a battery, an accumulator, a capacitor or fuel cell. The accumulator can be charged by induction by using an external inductive power source. The capacitor can be e.g. a so-called supercapacitor or electrical double-layer capacitor (EDLC) or "gold cap".

In again a further embodiment the accumulator is chargeable by induction or by energy harvesting, preferably by deriving thermal energy from a patient's body or kinetic energy from body movements of a patient.

In another embodiment the means for releasably affixing the housing to an implant comprise at least one fixing tab integral with or coupled to the housing. Therewith the advantage can be achieved that the fixing tabs can include screw holes so that the housing can comprise a hermetically sealed containment for the data processing device, the data memory and the data transmission device.

In another embodiment the at least one fixing tab comprises a through hole.

In a further embodiment the at least one fixing tab comprises a plurality of through holes for receiving a fastener. This configuration permits the advantage that different through hole configurations can serve different implant families with different hole patterns.

In again another embodiment the housing has an oblong shape with a first end, a second end, two long sides, an upper surface and a lower surface suitable for contacting a surface of an implant, wherein the housing additionally comprises at least one ridge which protrudes from the lower surface to establish contact to an implant and which extends transversally to the long sides. Therewith the advantage can be achieved that by fastening the housing to the implant, pretension is applied to the housing and to the sensor which improves the quality of the recorded signal.

In a further embodiment the means for releasably affixing the housing to an implant comprise at least one fastener or at least one cramp.

In a further embodiment the at least one cramp is integral with the housing.

In another embodiment the means for releasably affixing the housing to an implant comprise an external thread. Thus the housing can be configured as an end cap for an intramedullary nail, wherein the end cap comprises a section that is provided with the external thread suitable to threadably engage an internal thread in the rear section of the intramedullary nail.

In another embodiment the least one sensor is suitable to obtain measurement data related to at least one of the following physical quantities: load applied to an implant, strain in an implant and relative displacement of implant parts.

In a further embodiment the at least one sensor is selected from the following group of measuring probes: inductivity meters, capacitance meters, incremental meters strain gauges, particularly wire resistance strain gauges, load cells, Piezo based pressure sensors, accelerometers, gyroscopes, goniometers, magnetometers, temperature sensors. Temperature sensors can e.g. be used to identify infections in a patient's body. In again a further embodiment the data acquisition device additionally comprises a beeper or vibrator for event warning. The beeper or vibrator can be used as a real time excess load warning device.

In another embodiment the data acquisition device further comprises an actuator, preferably a distractor or a retractor.

In another embodiment the actuator is one of a piezo actuator, a motor and a heat generator. A heat generator can e.g. be used to trigger shape memory effects.

In another embodiment the implant is attachable to a bone and preferably comprises at least one screw hole suitable for receiving a bone fastener. By this means the advantage can be achieved that the complete data acquisition device can be attached to e.g. a bone plate at a desired position along the bone plate so that screws can be affixed in selectable plate holes of the bone plate.

In a further embodiment the kit further comprises at least one adapter suitable to be affixed in a screw hole of the implant and to receive a fastener for releasably affixing the housing to the implant.

In a further embodiment the adapter comprises an internal thread for threadably receiving a fastener.

In again a further embodiment the implant is a bone plate.

In another embodiment the one or more sensors are encapsulated in the housing.

In another embodiment the one or more sensors are attached to an inner wall of the housing.

In a further embodiment the implant is an intramedullary nail having a nail tip, a nail end and a central cannulation which is open at the nail end.

In a further embodiment the housing is configured as an end cap which is releasably fixable to the nail end of the intramedullary nail.

In another embodiment the one or more sensors are positionable in the central cannulation of the intramedullary nail and preferably electrically connected with the data acquisition device via a wire.

In another embodiment the one or more sensors are shaped and dimensioned to form a press fit with the central cannulation of the intramedullary nail.

In a special embodiment of the method the real-time processing under step B) is performed by employing one or several real-time min-max detectors with different sensitivity thresholds and respective peak counters.

In a further embodiment of the method the statistical data calculated in step C) includes the sum of maxima and minima and the peak counts in real-time based on the processed data obtained under step B).

In a further embodiment of the method in step D) the statistical data is automatically stored in the data memory at defined time points over the day-cycle or on manual request.

In another embodiment of the method in step A) the measurement data is continuously collected during a selectable period of time, preferably with a sampling frequency of 10-30 Hz.

Data acquisition can be interrupted when the patient sleeps, e.g. in the night during 4-8 hours to save energy.

The continuous recording of data additionally permits to determine patient activity, e.g. the number of steps per hour and the intensity distribution of the steps so as to generate an activity histogram. By this means a topical feedback related to the strain of the fracture can be obtained for the doctor and the patient so as to permit an active exerting of influence for the patient.

In a further embodiment of the method in step C) the statistical data is calculated by using evaluation intervals of minimum 4 hours, preferably of minimum 6 hours.

In a further embodiment of the method in step C) the statistical data is calculated by using evaluation intervals of maximum 48 hours, preferably of maximum 24 hours.

In again a further embodiment of the method in step C) the statistical data is automatically calculated in selectable evaluation intervals.

In another embodiment of the method in step E) the term for inquiring and downloading selected data is freely selectable by a user. By this means the advantage can be achieved that the patient can inquire and download data at any time or even withdraw from inquiring data for several weeks without losing data. The inquiry of data may be performed passively, e.g. via an automatic link acquisition of the smartphone once a week. Therewith the patient is independent of the clinic.

In another embodiment of the method the external data receiver is a smartphone suitably programmed to inquire and download data from the data acquisition device. The use of a smartphone permits the advantage that the external data receiver, i.e. the smartphone comprises a wireless internet connection to transmit data to an external computer.

In another embodiment of the method the external computer is configured as a webserver with a database for data collection.

In a further embodiment the method additionally comprises a calibration procedure before step A), wherein the calibration procedure comprises the steps of: i) Positioning a patient on a scale or on a force-plate; ii) Recording the load applied to the scale or on the force-plate; iii) Reading out the actual output of the sensor; iv) Calculating a linear calibration factor using the load recorded under step ii) and the actual output of the sensor read out under step iii); and v) Storing the linear calibration factor. The calibration procedure is necessary for interpretation of sensor data in terms of absolute values. The sensor output changes with the position of the sensor on the implant, the screw configuration of the implant, implant type, implant material etc.

In particular a medical device assembled from the kit according to the invention can be used for monitoring and/or controlling of bone healing in osteosynthesis.

Alternatively or additionally a medical device assembled from the kit according to the invention can be used for monitoring and/or controlling a bone distraction implant.

Another use of a medical device assembled from the kit according to the invention is its application in a telemetric implant system for performing the method according the invention, wherein the telemetric implant system may further comprise an external data receiver and an external computer.

Preferably, the external data receiver comprises a wireless internet connection. Furthermore, the external data receiver can be a smartphone and the external computer is preferably configured as a webserver with a database for data collection and personalized data access.

A BRIEF DESCRIPTION OF THE DRAWINGS

A special embodiment of the invention will be described in the following by way of example and with reference to the accompanying drawings in which.

DETAILED DESCRIPTION OF THE INVENTION

Figure 1:
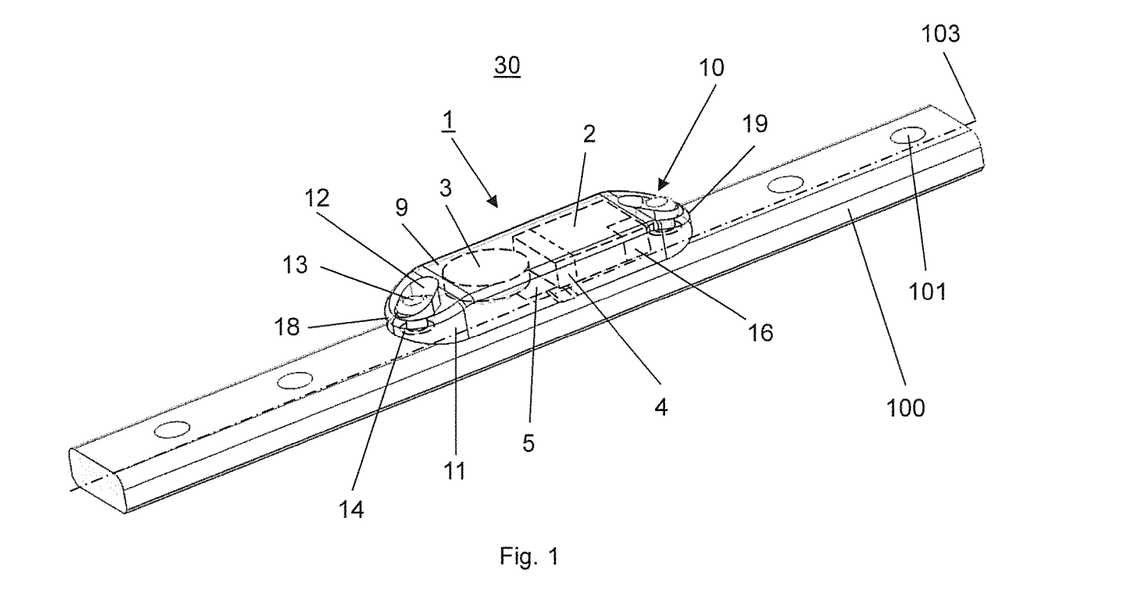
FIG. 1 illustrates a perspective view of an exemplary medical device assembled from an embodiment of the kit according to the invention.
Figure 2:
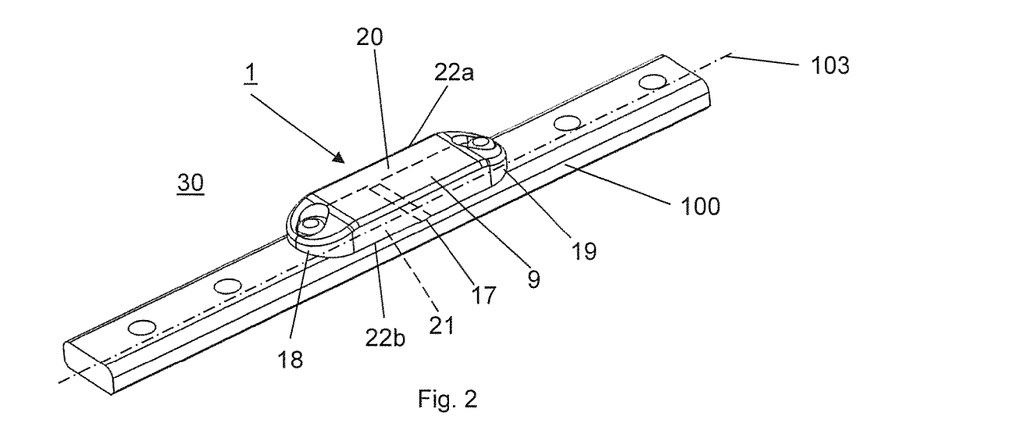
FIG. 2 illustrates a perspective view of the exemplary medical device according to FIG. 1.

FIGS. 1 and 2 illustrate a medical device 30 assembled from an embodiment of the kit according to the invention, wherein the assembled medical device 30 comprises an implant 100 which is configured exemplarily but not limiting as a bone plate, a data acquisition device 1 including a sensor 5 for an acquisition of measurement data related to one or more physical quantities acting upon the implant 100.

The data acquisition device 1 is implantable in a patient's body and essentially includes a sensor 5, an electronic data processing device 2 electrically connectable to the sensor 5, a data memory 16, a data transmission device 4 and a biocompatible sterilisable housing 9. Exemplarily but not limiting, the data acquisition device 1 further includes a clock to synchronize time points for data capture to the day cycle. The data memory 16 is electrically connected to the data processing device 2 and suitable to store data received from the data processing device 2 and the data transmission device 4 is electrically connected to the data memory 16. In the embodiment illustrated in FIG. 1 the housing 9 is configured to encapsulate at least the sensor 5, the data processing device 2, the data memory 16 and the data transmission device 4. Furthermore, the housing 9 comprises means 10 for releasably affixing the housing 9 to the implant 100. Preferably, the housing 9 is made of a biocompatible but non-biodegradable metallic or polymeric material, preferably of polyetheretherketone (PEEK) or polyetherketoneketone (PEKK). Furthermore, the housing 9 has an oblong shape with a first and a second end 18, 19 wherein the housing 9 is attached to the implant 100, i.e. the bone plate with the two long sides 22a, 22b of the housing 9 extending along a longitudinal axis 103 of the implant 100.

As illustrated in FIG. 1 the means 10 for releasably affixing the housing 9 to the implant 100 comprise exemplarily but not limiting two fixing tabs 11 which can be integral with the housing 9 an wherein each one of the fixing tabs 11 is arranged on one of the first and second ends 18, 19. Alternatively, the fixing tabs 11 can be separate parts which are coupled to the housing 9. Each of the fixing tabs 11 includes a through hole 12 for receiving a fastener 13, e.g. in the form of a screw to releasably affix the housing 9 to the implant 100. Due to this configuration the housing 9 can be configured as a hermetically sealed containment for the sensor 5, the data processing device 2, the data memory 16 and the data transmission device 4. The implant 100 of the medical device 30 assembled from an embodiment of the kit according to the invention as illustrated in FIGS. 1 and 2 is a bone plate comprising a number of screw holes 101 for receiving a bone screw to attach the bone plate to a bone.

Furthermore, the medical implant 100 comprises at least one adapter 14 inserted in a screw hole 101 of the implant 100 which is aligned with the through hole 12 in a fixing tab 11 arranged at the housing 9. The adapters 14 have an essentially hollow cylindrical shape and each adapter 14 is configured to be affixed in one of the screw holes 101 of the implant 100, e.g. by a press-fit or by a threaded engagement. Exemplarily but not limiting each adapter 14 comprises an internal thread for threadably engaging the fastener 13 so as to releasably affix the housing 9 to the implant 100, i.e. the bone plate.

Figure 3:
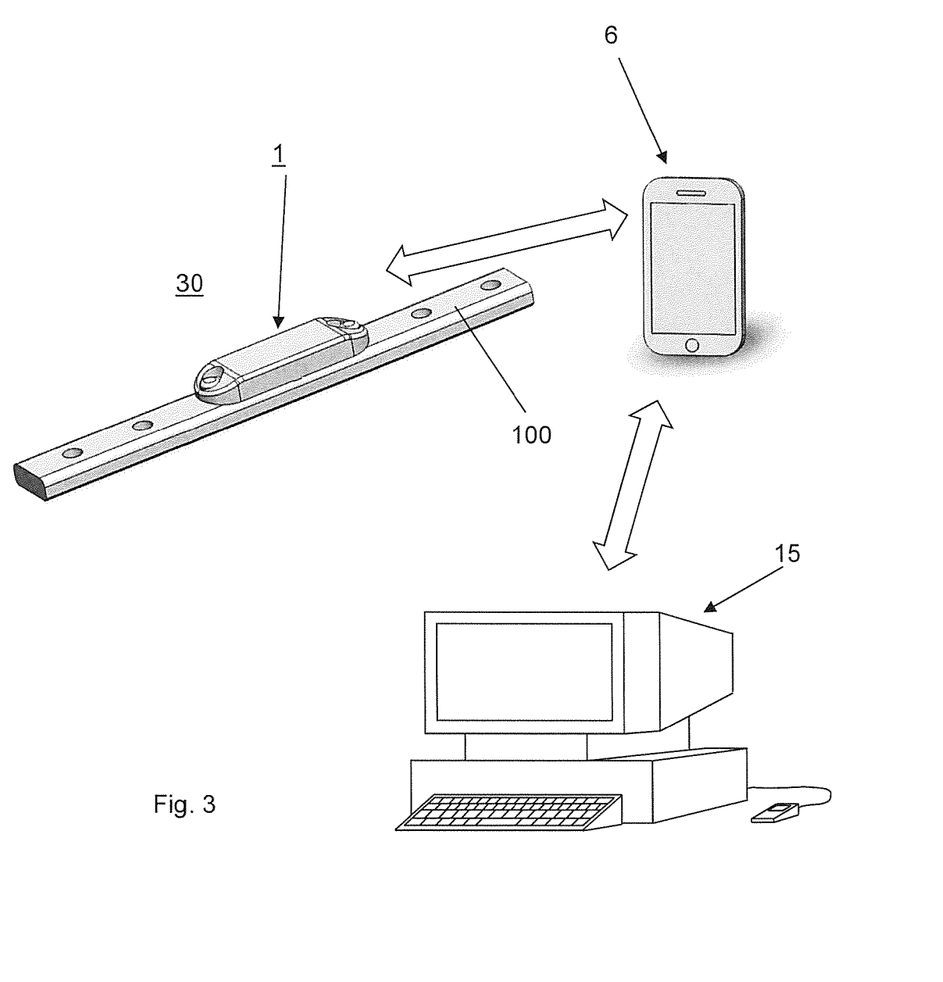
FIG. 3 illustrates a schematic view of a telemetric implant system for monitoring and/or controlling of a medical implant being part of the medical device according to FIGS. 1 and 2.

The housing 9 comprising the complete data acquisition device 1 can be attached to the implant 100, i.e. the bone plate at a desired position along the bone plate. The adapters 14 can be inserted in selectable screw holes 101 of the implant 100 so that the fasteners 13 for affixing the housing 9 to the implant 100 can be affixed in selectable plate holes of the bone plate which are not used to fasten the implant 100 to a bone. Exemplarily but not limiting the data acquisition device 2 includes a data transmission device 4 which is configured as a wireless data transmitter based on a wireless technology standard, preferably Bluetooth or NFC. If the Bluetooth or NFC standard is used the external data receiver 6 can be a commercially available smartphone as illustrated in FIG. 3.

Alternatively, a radio frequency identification device (RFID) may be used where no internal energy is needed, since the process is fed by induction from outside. Typical data volumes to be transmitted by RFID range between Bytes and 1 kB. Furthermore, the required space for the transponder is minimal and the transmission process is fast and simple.

Furthermore, the data transmission device 4 can be actuated by the external data receiver 6 to transmit selected data stored in the data memory 16 and the data processing device 2 may be programmable via the external data receiver 6.

The data acquisition device 1 further comprises a power supply 3 which can be a battery, an accumulator, a capacitor or a fuel cell, wherein the accumulator may be e.g. configured to be charged by induction by using an external inductive power source. Alternatively, the accumulator may be configured to be chargeable by energy harvesting, e.g. by deriving thermal energy from a patient's body or kinetic energy from body movements of a patient.

As illustrated in FIG. 1 the data acquisition device 1 comprises a sensor 5, which is, exemplarily but not limiting, suitable to obtain measurement data related to load applied to the implant 100 and/or implant strain. In this case the sensor 5 may be a strain gauge, in particular a wire resistance strain gauge that can be attached to, e.g. glued on the inner wall of the biocompatible housing 9.

Depending on the application of the medical implant other types of sensors 5 may be used, for instance inductivity meters, incremental meters, capacitance meters, load cells, Piezo based pressure sensors, accelerometers, gyroscopes, goniometers, magnetometers, temperature sensors.

As illustrated in FIG. 2, the housing 9 has an oblong shape with a first end 18, a second end 19, two long sides 22a, 22b, an upper surface 20 and a lower surface 21, wherein the housing 9 is attached to the implant 100, i.e. the bone plate with the two long sides 22a, 22b of the housing 9 extending in the direction of the longitudinal axis 103 of the implant 100. Exemplarily but not limiting the housing 9 additionally comprises one ridge 17 which protrudes from the lower surface 21 and which extends transversally to the long sides 22a,b. The ridge 17 contacts the upper surface of the implant 100 and is arranged exemplarily but not limiting in the middle of the housing 9 between the first and second ends 18, 19. By fastening the housing 9 to the implant 100, the first and second ends 18, 19 are pressed against the upper surface of the implant 100 resulting in a pretension applied to the housing 9 and to the sensor 5 due to the ridge 17. In a particular configuration of the sensor 5 as a strain gauge the quality of the recorded signal even in case of a small stretching is improved.

Additionally, the data acquisition device 1 may comprise a beeper or vibrator for event warning to be used e.g. as a real time excess load warning device. Furthermore, the data acquisition device 1 may comprise an actuator, exemplarily but not limiting a distractor or a retractor. The actuator may be one of a piezo actuator, a motor and a heat generator, wherein the latter can e.g. be used to trigger shape memory effects of implants made of a memory alloy.

The data processing device 2 is particularly programmed to calculate statistical data based on measurement data retrieved from the data memory 16 and to store the statistical data in the data memory 16. In order to use the data acquisition device 2 for monitoring and/or controlling the implant 100 the statistical data calculated by the data processing device 2 exemplarily but not limiting comprises the sum of the measured values, the number of measured values, average value, minimal value and maximal value.

Furthermore, the data processing device 2 is programmed for continuous data collection within a selectable period of time. There may be different modes to save energy up to only 4 h data capture during midday or to exclude e.g. sleeping periods of 4-8 hours during the night. The required statistical data is calculated by means of the data processing device 2 by using selectable averaging intervals of exemplarily but not limiting between 4 hours and 24 hours. Preferably, the data processing device 2 is programmed to automatically calculate the statistical data in a selected averaging interval.

FIG. 3 illustrates a telemetric implant system including the medical device 30 of FIG. 1, an external data receiver 6 and an external computer 15, wherein the system of FIG. 3 is configured for monitoring and/or controlling the implant 100 of the medical device 30 by performing an embodiment of the method according to the invention. Exemplarily but not limiting the external data receiver 6 is a smartphone comprising a wireless internet connection and the external computer 15 is configured as a webserver with a database for data collection and personalized data access. The telemetric implant system of FIG. 3 permits a continuous acquisition of measurement data at a remote location and a transmission of data related to the measurement data to an external computer 15 to provide a centralized data base.

A preferred embodiment of the method for monitoring and/or controlling an implant 100 essentially comprises the following steps: A) obtaining measurement data by means of the sensor 5; B) performing real-time processing on the measurement data obtained under step A) by e.g. employing one or several real-time min-max detectors with different sensitivity thresholds and respective peak counters; C) calculating statistical parameters, such as the sum of maxima and minima and the peak counts in real-time based on the processed data under step B); D) automatically storing the statistical parameters in the data memory 16 at defined time points over the day cycle or on manual request; E) inquiring and downloading selected data stored in the data memory 16 by means of an external data receiver 6; and F) transmitting the downloaded selected data from the external data receiver 6 to an external computer 15 for further data management and processing. The patient data can be exemplarily but not limiting recorded and analysed in the central computer 15 to efficiently produce statistical reference plots to improve the interpretation of the data. If a determination of the patient's activity is of interest, e.g. the number of steps per hour and the intensity distribution of the steps an activity histogram can be generated on the basis of the continuously recorded data. By this means a topical feedback related to the strain of the fracture can be obtained for the doctor and the patient so as to permit an active exerting of influence for the patient. For this reason in step A) the measurement data is preferably continuously collected during a selectable period of time, preferably with a sampling frequency of 10-30 Hz.

Due to a selected evaluation interval between 4 hours and 24 hours for calculating the required statistical data by means of the data processing device 2 the data to be transmitted via the data transmission device 4 to an external data receiver 6 can be significantly reduced. By this means, the energy demand for data transmission can be reduced which usually is the major part of the energy consumption of the data acquisition device 2 so that an autonomous operation of the data acquisition device 1 during at least four months can be achieved.

The patient can inquire and download data at any time or even withdraw from inquiring data for several weeks without losing data. The external data receiver 6 may be a smartphone suitably programmed to inquire and download data from the data acquisition device 1. The inquiry of data may be performed passively, e.g. via an automatic link acquisition of the smartphone once a week so as to permit the patient to be independent of the clinic. Therefore, in step E) the term for inquiring and downloading selected data is freely selectable by a user.

Exemplarily but not limiting an external data processing can be performed as follows: The data may be either downloaded and stored on the external computer or directly processed in the data receiving device 6, e.g. a smartphone. The sum of sensor response is calibrated to actual units using a linear approach by utilizing a predefined or patient specific scale factor. Subtracting the values of the previous time point from the actual values delivers information about the current period. The sample count divided by the sample frequency provides the running time. The cumulated amplitude from peak detection divided by the number of physiological load cycles represents a measure for the sensor response per load cycle.

Meaning of the Results and Presentation:

The mentioned evaluations may be visualized by plotting the measured and processed values over time in absolute or relative terms (normalizing the sensor response to the initial postoperative response of the sensor). For instance, the healing process may be visualized with decreasing average amplitude from peak-valley detection over time. A threshold can be set for determining the optimal time point for implant removal. Mal-unions may be identified at an early stage and different dynamization protocols can be evaluated. The progression of the number of physiological load cycles in different intensities obtained from a multitude of peak-valley detectors gives information about the patients activity over time and therefore about the stimulation of the bone. For monitoring distraction implants, the current sensor value provides valuable information about the progression of the distraction process.

Figure 4:
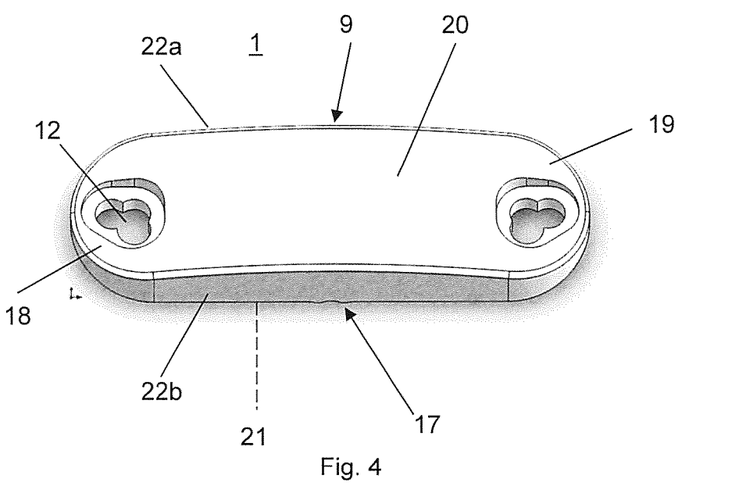
FIG. 4 illustrates a perspective view of a further exemplary medical device assembled from an embodiment of the kit according to the invention.

FIG. 4 illustrates a housing 9 of the data acquisition device 1 of another embodiment of the kit according to the invention, wherein the housing 9 of FIG. 4 differs from the housing 9 of the embodiment of FIGS. 1 to 3 only therein that it comprises two parallel ridges 17 to generate a constant bending moment in-between both ridges 17 (as present in a 4-point bending case) to provide improved mechanical conditions to the above mounted sensors 5 and that the through holes 12 arranged at the first and second ends 18, 19 of the housing 9 are configured as a combination of holes. The two ridges 17 protrude from the lower surface 21 and extend transversally to the long sides 22a,b of the housing 9. Exemplarily but not limiting the through holes 12 comprise three overlapping bore holes so as to form the clover-leaf like cross sectional area to permit a fixation of the housing 9 on a variety of implants.

Figure 5:
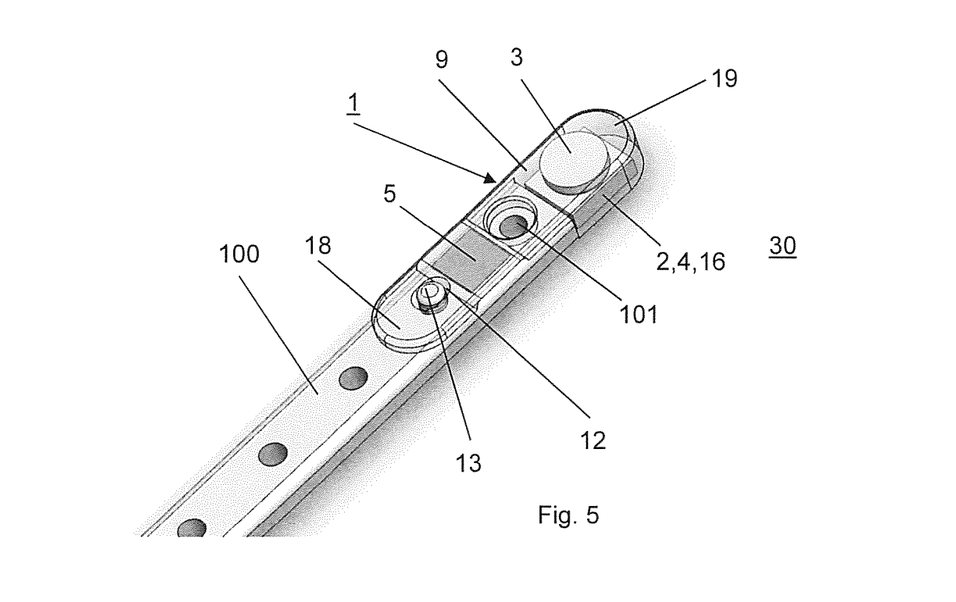
FIG. 5 illustrates a perspective view of another exemplary medical device assembled from an embodiment of the kit according to the invention.

In FIG. 5 a data acquisition device 1 of another embodiment of the kit according to the invention is illustrated, wherein the data acquisition device 1 of FIG. 1 differs from the data acquisition device 1 of the embodiment of FIGS. 1 to 3 only therein that the housing 9 has a stepped configuration so that the data acquisition device 1 can be arranged on one end of the bone plate, i.e. the implant 100. Due to this stepped configuration the housing 9 has a recess forming a shoulder that can be pressed against the end surface of the bone plate, i.e. the implant 100 in the case that the terminal screw hole 101 of the implant 100 cannot be used to affix the housing 9 to the implant 100, e.g. in the case of a use of locking bone screws. Thereto, a first portion of the housing 9 in the range of the first end 18 has a small height protruding over the top surface of the implant 100 and a second portion of the housing 9 in the range of the second end 19 has a larger height which coincides with the sum of the heights of the first portion and the implant 100. The second portion of the housing 9 extends from the end of the implant 100 and exemplarily but not limiting encapsulates the data processing device 2, the data transmission device 4, the data memory 16 and the power supply 3. The sensor 5 is arranged in the first portion of the housing 9 which covers an end portion of the implant 100. Furthermore, the through hole 12 is arranged in the first portion of the housing 9 so that the fastener 13 can be inserted in a screw hole 101 of the implant 100 as described above. Preferably, the terminal screw hole 101 of the implant 100 is used for insertion of a bone screw (not shown). Thereto, the first portion of the housing 9 comprises an opening penetrating through the first portion.

Figure 6:
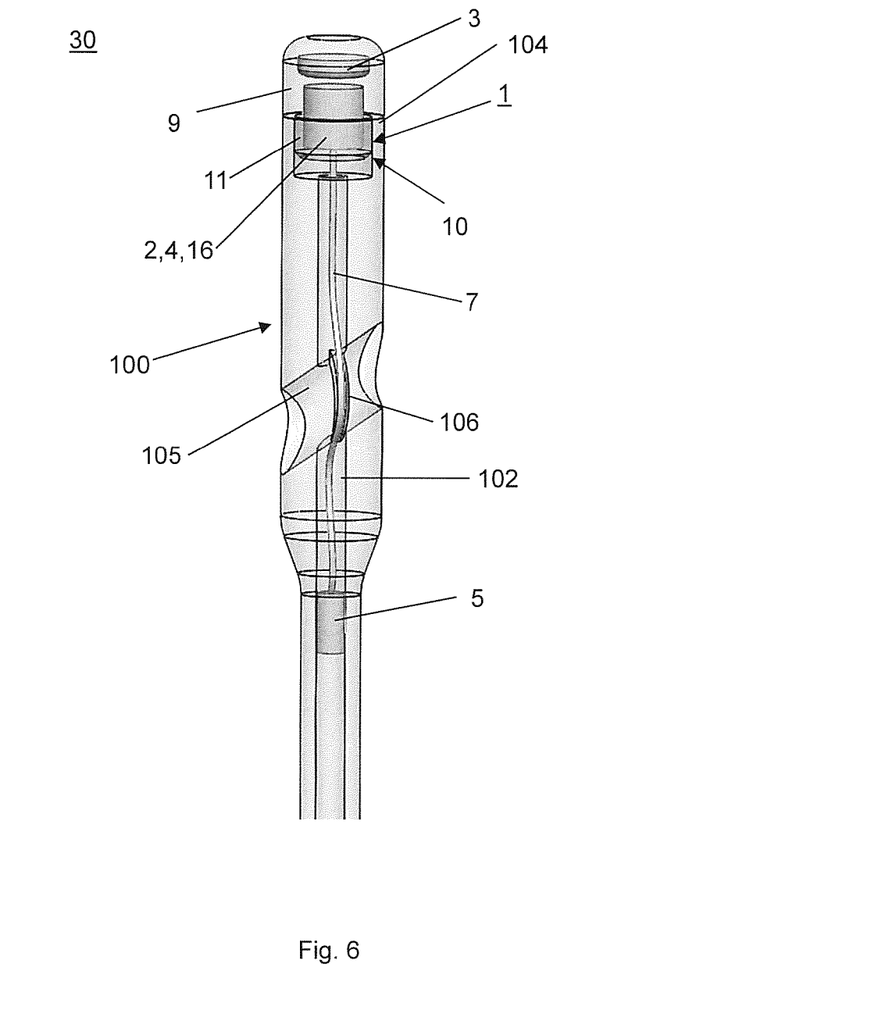
FIG. 6 illustrates a perspective view of again another embodiment of the medical device assembled from an embodiment of the kit according to the invention.

FIG. 6 illustrates a medical device 30 assembled from another embodiment of the kit according to the invention which differs from the embodiment of FIGS. 1 to 5 only therein that the implant 100 is an intramedullary nail having a nail tip, a nail end 104, a transverse hole 105 in a rear portion of the intramedullary nail, i.e. the implant 100 and a central cannulation 102 which is open at the nail end 104. The housing 9 is configured as an end cap which is releasably fixable to the nail end 104 of the intramedullary nail. Exemplarily but not limiting the means 10 for releasably affixing the housing 9 to an implant 100 comprise an external thread at a front section of the end cap so as to threadably engage an internal thread in the rear section of the intramedullary nail. The sensor 5 is positionable in a surgeon selected position in the central cannulation 102 of the intramedullary nail and is fixed to the implant 100 via a pressfit between the sensor 5 and the central cannulation 102. Furthermore, the sensor 5 is electrically connected with the data acquisition device 1 via a wire. Exemplarily but not limiting the intramedullary nail, i.e. the implant 100 comprises a groove 106 penetrating into the peripheral wall of the transverse hole 105 so as to receive the wire 7 when a locking screw or a hip screw is inserted into the transverse hole 105 to prevent interference between the wire 7 and a locking screw or hip screw.

Application examples of the medical device according to the invention:

1) Monitoring of bone healing in osteosynthesis following the principle of secondary healing. The strain in a standard bone plate or intramedullary nail measured by strain gauges could be acquired and processed with the data acquisition device 1. Reduction of strain could be interpreted as enhanced load sharing of the bone and as progress in the bone consolidation. Knowledge about the healing progression is valuable information to detect mal-unions at an early stage or to determine an optimal time-point for implant removal.

Mechanical stimulation of bone is known to promote bone formation. A tool to monitor dynamization of newly proposed dynamic implants and its progression over time is also an application field for the data acquisition device 1. It offers the opportunity to acquire long term data rather than repeated short term measurements as done by known techniques.

2) Monitoring of a distraction implant. The method of distracting bone is used for generation of new bone tissue for critical size defects or bone lengthening. The exact telescoping of the implant, like an intramedullary distraction nail is essential to know for optimized bone generation. The data acquisition device 1 can be used for transmitting the current distraction of the implant as well as the progression of the distraction over time.

Additional or alternative application examples may be:

Measurement of blood sugar and counteraction by controlled release of Insulin. Blood sugar values are monitored and processed over a certain time period and used for controlling deliverance of medication. This can be realized as autonomous control loop inside the body. The values have to be transferred to an external receiver to control the process.

Arterial blood gas monitoring ($O_2$, $CO_2$, blood pressure)

Lactate concentrations

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

The invention claimed is:

1. A kit comprising:
   a medical implant; and
   a data acquisition device which comprises:
     one or more sensors;
     an electronic data processing device electrically connectable or connected to the one or more sensors;
     a data memory electrically connected to the data processing device and configured to store data received from the data processing device; and
     a data transmission device electrically connected to the data memory, a biocompatible sterilisable housing encapsulating at least the data processing device, the data memory and the data transmission device; and
     means for releasably affixing the housing to the implant;
   wherein the means for releasably affixing the housing to an implant comprises at least one fixing tab integral with or coupled to the housing;
   wherein the data processing device is programmed to calculate statistical data based on measurement data received from the one or more sensors and to store the statistical data in the data memory; and
   wherein:
   the one or more sensors are either arranged in the housing; or
   the one or more sensors are separately fixable to the implant in a selectable position.

2. The kit according to claim 1, wherein the data processing device is programmed for continuous data collection within a selectable period of time.

3. The kit according to claim 1, wherein the data acquisition device additionally includes an internal clock.

4. The kit according to claim 1, wherein the data processing device is programmed to calculate the statistical data by using evaluation intervals of 4 or more hours.

5. The kit according to claim 1, wherein the housing is made of a biocompatible but non-biodegradable metallic or polymeric material.

6. The kit according to claim 1, wherein the data acquisition device further comprises a power supply.

7. The kit according to claim 1, wherein the at least one fixing tab comprises a through hole.

8. The kit according to claim 1, wherein the means for releasably affixing the housing to the implant comprises at least one fastener or at least one cramp.

9. The kit according to claim 1, wherein the least one sensor is configured to obtain measurement data related to at least one physical quantity selected from a group consisting of load applied to the implant, strain in the implant and relative displacement of parts of the implant.

10. The kit according to claim 1, wherein the at least one sensor is selected from a group consisting of measuring probes, inductivity meters, capacitance meters, incremental meters, strain gauges, load cells, Piezo based pressure sensors, accelerometers, gyroscopes, goniometers, magnetometers, and temperature sensors.

11. The kit according to claim 1, wherein the implant comprises at least one screw hole for receiving a bone fastener.

12. The kit according to claim 11, further comprising at least one adapter configured to be affixed in a screw hole of the implant and to receive a fastener for releasably affixing the housing to the implant.

13. The kit according to claim 12, wherein the adapter comprises an internal thread for threadably receiving the fastener.

14. The kit according to claim 1, wherein the implant is a bone plate.

15. The kit according to claim 1, wherein the one or more sensors are encapsulated in the housing.

16. The kit according to claim 15, wherein the one or more sensors are attached to an inner wall of the housing.

17. A method for monitoring and/or controlling a medical implant being part of a medical device assembled from a kit according to claim 1, the method comprising steps:
   A) obtaining measurement data by means of the sensor;
   B) performing real-time processing on the measurement data obtained under step A) and by means the data processing device;
   C) calculating statistical data based on the processed data under step B);
   D) storing the statistical data in the data memory;
   E) inquiring and downloading selected data stored in the data memory by means of an external data receiver; and
   F) transmitting the downloaded selected data from the external data receiver to a computer for further data management and processing.

18. The method according to claim 17, wherein the real-time processing under step B) is performed by employing one real-time min-max detector.

19. The method according to claim 17, wherein the statistical data calculated in step C) includes the sum of maxima and minima and peak counts in real-time based on the processed data obtained under step B).

20. The method according to claim 17, wherein the real-time processing under step B) is performed by employing several real-time min-max detectors with different sensitivity thresholds and respective peak counters.

* * * * *